United States Patent [19]
Coelho et al.

[11] Patent Number: 5,759,171
[45] Date of Patent: Jun. 2, 1998

[54] SPRAYER FOR FIBRIN GLUE

[75] Inventors: Philip H. Coelho, Dorado Hills; Terry L. Wolf, Placerville; Peter Menke, Antelope; Jerry M. Alcone, Rancho Cordova, all of Calif.

[73] Assignee: ThermoGenesis Corp., Rancho Cordova, Calif.

[21] Appl. No.: 722,473

[22] Filed: Sep. 27, 1996

[51] Int. Cl.$^6$ .................................................. A61M 37/00
[52] U.S. Cl. .................................... 604/82; 239/419.3
[58] Field of Search .................................. 604/46, 49, 56, 604/82, 83, 94, 173, 181, 187, 191, 258, 390, 311; 606/213, 214; 239/398, 418, 419, 419.3, 423; 222/129, 135, 137

[56] References Cited

U.S. PATENT DOCUMENTS

| | | |
|---|---|---|
| D. 369,657 | 5/1996 | McGugan. |
| 3,269,389 | 8/1966 | Meurer et al.. |
| 4,040,420 | 8/1977 | Speer .................. 604/191 |
| 4,359,049 | 11/1982 | Redl et al.. |
| 4,659,677 | 4/1987 | Glover et al. .............. 604/56 |
| 4,874,368 | 10/1989 | Miller et al.. |
| 4,902,281 | 2/1990 | Avoy. |
| 5,104,375 | 4/1992 | Wolf et al.. |
| 5,116,315 | 5/1992 | Capozzi et al.. |
| 5,240,146 | 8/1993 | Smedley et al.. |
| 5,253,785 | 10/1993 | Haber et al.. |
| 5,271,527 | 12/1993 | Haber et al.. |
| 5,286,258 | 2/1994 | Haber et al.. |
| 5,290,259 | 3/1994 | Fischer. |
| 5,314,412 | 5/1994 | Rex. |
| 5,318,524 | 6/1994 | Morse et al.. |
| 5,322,510 | 6/1994 | Lindner et al.. |
| 5,330,079 | 7/1994 | Keller. |
| 5,330,974 | 7/1994 | Pines et al.. |
| 5,336,202 | 8/1994 | Bailly et al. .............. 604/258 |
| 5,368,563 | 11/1994 | Lonneman et al.. |
| 5,378,233 | 1/1995 | Haber et al.. |
| 5,405,607 | 4/1995 | Epstein. |
| 5,419,491 | 5/1995 | Breitsprecher ........... 239/419.3 |
| 5,423,752 | 6/1995 | Haber et al.. |
| 5,464,396 | 11/1995 | Barta et al.. |
| 5,474,540 | 12/1995 | Miller et al.. |
| 5,505,704 | 4/1996 | Pawelka et al.. |
| 5,605,541 | 2/1997 | Holm. |

Primary Examiner—Michael Buiz
Assistant Examiner—Kevin Troung
Attorney, Agent, or Firm—Bernhard Kreten

[57] ABSTRACT

A sprayer for dispensing fibrinogen and thrombin to form fibrin glue immediately away from the sprayer to prevent clogging and insure accurate precise metering. The sprayer includes a pistol grip area, a barrel and a trigger which moves a plunger support that captures the plunger of a syringe. One syringe holds thrombin and the other syringe holds fibrinogen. Each syringe communicates with an outlet having an atomizer.

41 Claims, 5 Drawing Sheets

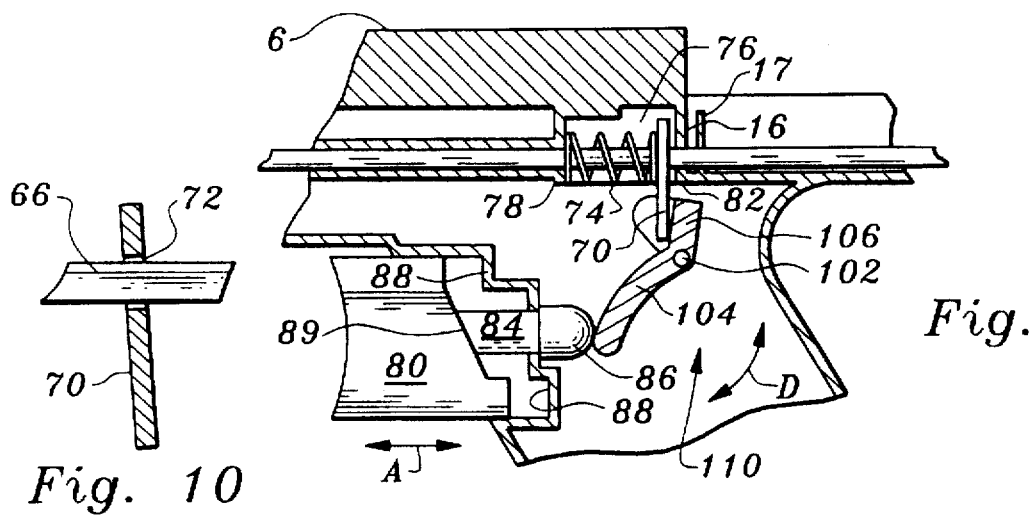
Fig. 9
Fig. 10
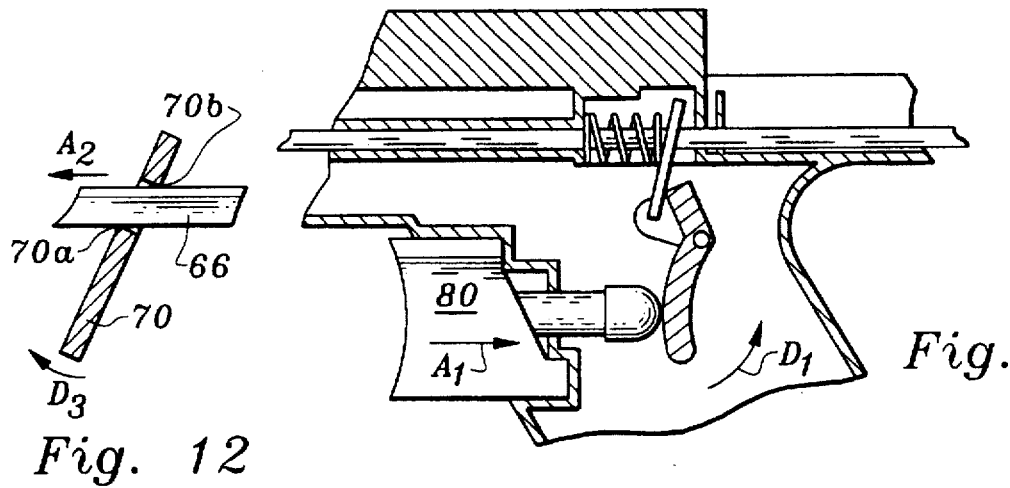
Fig. 11
Fig. 12
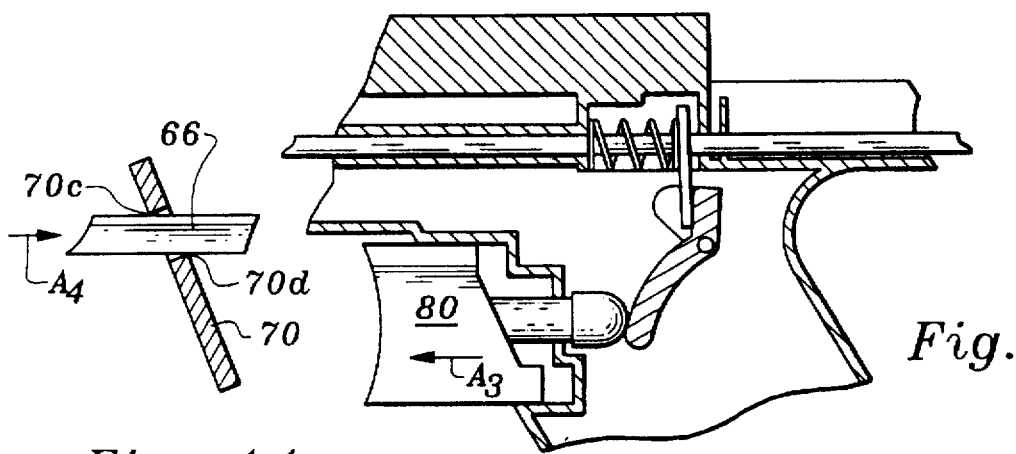
Fig. 13
Fig. 14

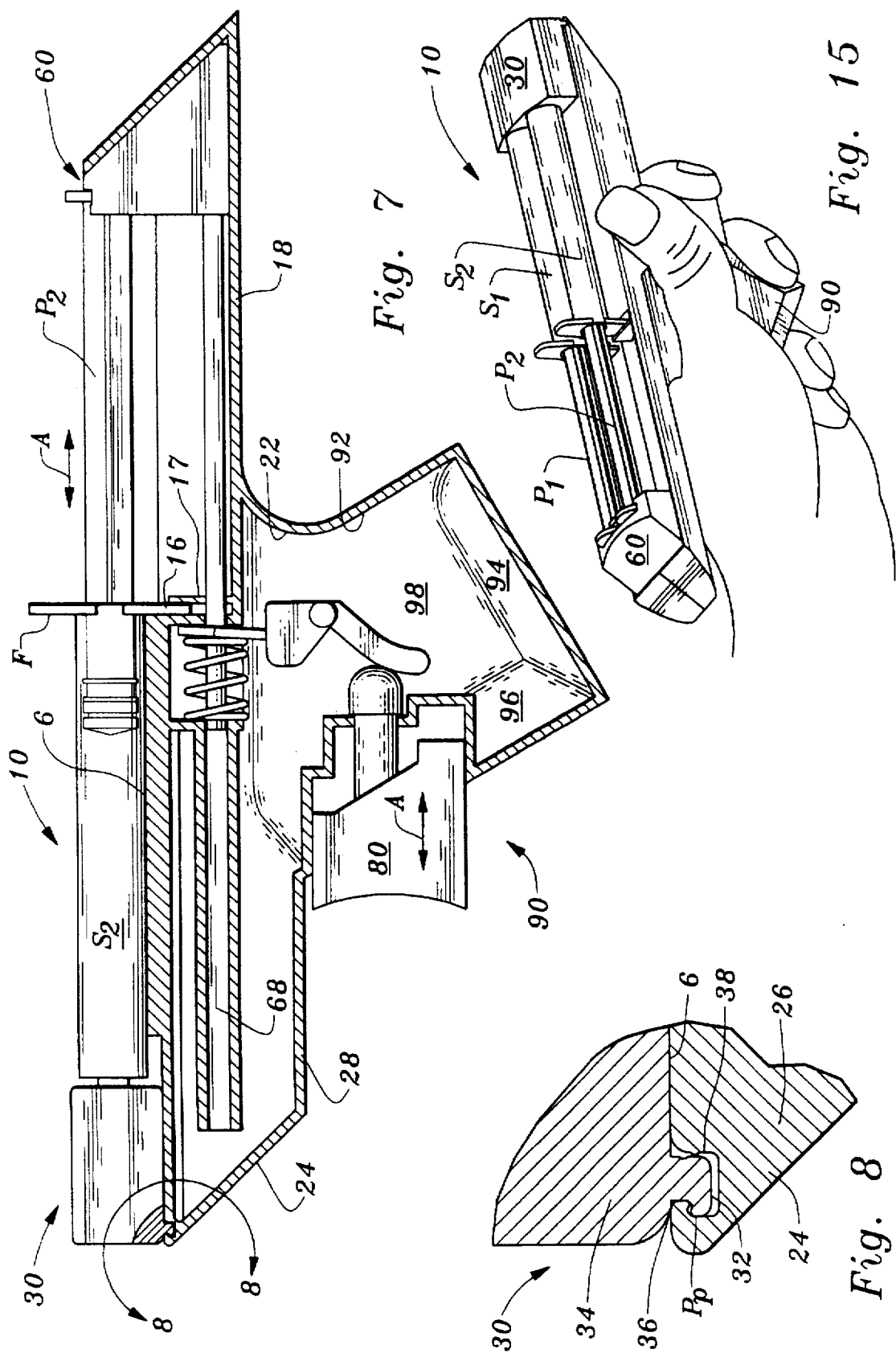

SPRAYER FOR FIBRIN GLUE

FIELD OF THE INVENTION

The following invention relates generally to instrumentalities and methodologies for dispensing two discrete components each as a spray, which, when mixed, react and form a biological adhesive. More specifically, the instant invention is directed to a spraying apparatus and methodology for dispensing fibrin glue by the strategic admixture of thrombin from one source and fibrinogen from another source.

BACKGROUND OF THE INVENTION

Dispensers for fibrin glue should be easy to handle, non clogging, exhibit minimal ullage and be precise in their ability to place and meter the fibrin glue at the desired site. To date, all prior art dispensers have been deficient in one or more of the above areas. Because fibrinogen, which is used to produce the fibrin glue is a relatively precious commodity, especially when the fibrinogen is derived autologously, it is imperative that the maximum efficiency possible be experienced when dispensing fibrin glue.

Precise metering has been the bane of devices which dispense fibrin glue. Metering implies that both the precise quantity of fibrin glue will be dispensed and delivered strategically to the appropriate site. Because the glue can obstruct passageways, volume variations which lead to clogging have been a recurring problem.

Impediments that exacerbate the foregoing problems include lack of an ergonomically designed dispensing tool which would facilitate usage in a natural, intuitive way. If the dispensing tool cannot be conveniently grasped, the product being delivered is less likely to be accurately deployed either to the right site or in the right amount.

Another vexing, recurring problem in mixing two component compounds involves the strategic blending of the two components at the appropriate location. A chemical process is associated with mixing the two components. Timing and location are critical. Otherwise, the chemical reaction will likely occur at an unwanted location at an unwanted time. Since fibrin glue is formed substantially immediately upon the contact of thrombin with fibrinogen, and because fibrin glue sets up almost immediately upon its formation, clogging of a dispensing tool can occur. During a surgical procedure, when fibrin glue is used to stem the flow of blood, malfunctions of a fibrin glue delivering tool can have adverse consequences. One corollary to the problem of clogging involves the fact that the thrombin and fibrinogen are typically loaded into the dispensing device with syringes. Should a clog occur, either the dispensing instrumentality has to be cleaned or replaced under aseptic conditions since the fibrinogen and thrombin earmarked for that procedure should be salvaged if at all possible.

It requires that initially the user's thumb be fully extended to engage a moveable plunger while the index finger and middle finger engage purchase areas on the body of the dispenser. A spray mist requires forceful movement of the thumb towards the index and middle finger. This motion makes it difficult to precisely control the spray site and amount and is ergonomically inefficient.

SUMMARY OF THE INVENTION

The instant invention is distinguished over the known prior art in a multiplicity of ways. For example, the instant invention is distinguished over the known prior art by having an ergonomically designed contour to allow the user of the device ready control over dispensing the fibrin glue both as to the site and amount.

One hallmark of the instant invention involves a "pistol grip" type of dispenser in which two syringes, one carrying thrombin, the other carrying fibrinogen are loaded in spaced parallel relationship into a barrel portion of a dispensing tool which is evocative of a pistol. The two syringes are in operative communication with a pair of spray nozzles oriented to spray each liquid under the impetus of a trigger. Each spray nozzle sends a fine, atomized mist in a diverging conical pattern. The trajectory of one spray overlaps the other approximately 2.65 inches from the tip of the nozzle.

The trigger of the dispensing tool is manipulated by an index finger of the surgeon and the hand hold area ("pistol grip") for the device is preferably short to allow clearance so that the dispenser can be used in areas involving tight clearances (e.g. internal body cavities). Unlike prior art devices where the syringes are pushed in a conventional syringe manner (i.e. the thumb on the syringe plunger is extended, pushing the plunger towards the index finger and middle finger of the hand which holds the syringe barrel in a typical syringe motion), the structure according to the instant invention lends itself to a more natural ergonomic motion by the hand so as to provide better control of the spray.

In addition, the mechanism incorporating the spray dispensation ensures a uniform dosage will be sprayed upon each manipulation of the spray trigger. This type of standardization allows a known amount of fibrin glue to be dispensed on each spray actuation.

Because thrombin and fibrinogen are highly reactive, contact between the two components at dispensing areas on prior art devices caused instant clogging. The instant invention includes means to make less likely the instances of clogging, and should clogging occur, remedies to unclog quickly are provided.

One remedy involves the trigger. The trigger mechanism, besides precisely metering out spray, includes structure which allows the pressure exerted on the syringes containing thrombin and fibrinogen to be "backed off" or allowed to creep back to a hydrostatically unstressed position so that it is less likely substance will leak or ooze from the syringes, thereby avoiding a potential source of contamination.

Moreover, the trigger requires a small, natural motion of the surgeon's index finger. The mechanism coupled to the trigger amplifies the trigger motion to produce a predictable, powerful spray with minimal effort, allowing the surgeon control, ease of use and precision.

In addition, a second remedy designs the spray heads as modular and are therefore easily replaceable from the spray head assembly. These factors coupled with a short pistol grip and ergononic deployment make a user friendly device.

OBJECTS OF THE INVENTION

Accordingly, it is a primary object of the present invention to provide a new and novel fibrin glue sprayer.

A further object of the present invention is to provide a device as characterized above which is ergonomically sound affording precise control at all times.

A further object of the present invention is to provide a device as characterized above which allows a trigger mechanism to amplify a surgeon's modest movement of the trigger using an index finger, thereby providing a strong spray of predictable characteristics.

A further object of the present invention is to provide a device as characterized above which has a compact profile to allow access of the sprayer into areas normally difficult to access.

A further object of the present invention is to provide a device as characterized above which minimizes the instances of and effects of inadvertent mixing of the reactive components used in the spray device.

A further object of the present invention is to provide a device as characterized above in which finally atomized mists of the two components are caused to focus a precise distance from the nozzles in an overlying concentric, conical pattern for efficient admixture of the two components of the system.

A further object of the present invention is to provide a device as characterized above wherein the components associated with the instant invention lend themselves to mass production techniques and can benefit from manufacturing economies of scale thereby so that should it be economically desirable, the device can be economically disposed after a single use.

A further object of the present invention is to provide a device as characterized above in which the core components of the device are durable and can be readily autoclavable to reprovide aseptic conditions.

Viewed from a first vantage, it is an object of the present invention to provide an: apparatus for dispensing fibrin glue formed from thrombin and fibrinogen, where both the thrombin and the fibrinogen are respectively sequestered in independently operable syringes, the syringes each having a plunger which reciprocate within a hollow syringe and an outlet on the syringe body remote from the plunger, including: means for supporting each of the syringes on a barrel portion of the spray gun, means for constraining plungers of each syringe such that each plunger can reciprocate within a respective hollow of its syringe, said plunger constraining means operatively coupled to a trigger including metering means to carefully control the degree to which the plungers are depressed within the hollows of the syringes to precisely meter the outflow from each syringe, and first and second spray means, one for each syringe, and one said spray means operatively coupled to the outlet of one syringe whereby actuation of the plunger through the trigger dispenses the contents of each said syringe in a fine mist.

Viewed from a second vantage point, it is an object of the present invention to provide a method for forming fibrin glue, the steps including sequestering thrombin in a first syringe, sequestering fibrinogen in a second syringe, orienting each said syringe to be in fluid communication with its own spray head, coupling plungers of each said syringe to a plunger pusher, coupling the plunger pusher to a trigger and metering the fluid exiting each syringe by the trigger.

Viewed from a third vantage point, it is an object of the present invention to provide fibrin glue formed from the coaction of two fine mists: each mist diverges outwardly and each overlaps the other a set distance from its launching source, the fibrin glue formed by a first mist of thrombin projected as an atomized mist in an outwardly diverging pattern from a thrombin source, fibrinogen embodied as a second mist and projected from a fibrinogen source and projected in an outwardly diverging pattern, the first and second outwardly diverging patterns having means to overlap each other during a portion of the respective trajectories remote from sites of spraying so that the thrombin and fibrinogen can mix while aloft and land on a target in substantially overlapping patterns.

These and other objects will be made manifest when considering the following detailed specification when taken in conjunction with the appended drawing figures.

BRIEF DESCRIPTION OF THE DRAWINGS

FIG. 7 is a sectional view along a vertical plane centerline of that which is shown in FIG. 2.

FIG. 8 is a further detail of the tip area showing its ability to hinge from a first position shown in FIG. 4 to a second position shown in FIG. 3.

FIG. 9 is a detail of the trigger mechanism in a first, at rest position.

FIG. 10 is an exaggerated detail of the wobble plate shown in FIG. 9 in an at rest position.

FIG. 11 is a view similar to FIG. 9 showing the trigger in a deployed position and its effect on the wobble plate.

FIG. 12 is an exaggerated view of the effect on the wobble plate in FIG. 11.

FIG. 13 is a view of the trigger in a relaxed position showing the wobble plate returning to the FIGS. 9 and 10 position.

FIG. 14 is an exaggerated view of the wobble plate of FIG. 13 showing its ability to cause "creep back" of the plunger assembly.

FIG. 15 is a perspective view of the sprayer being held to be used.

DESCRIPTION OF PREFERRED EMBODIMENTS

Figure 1:
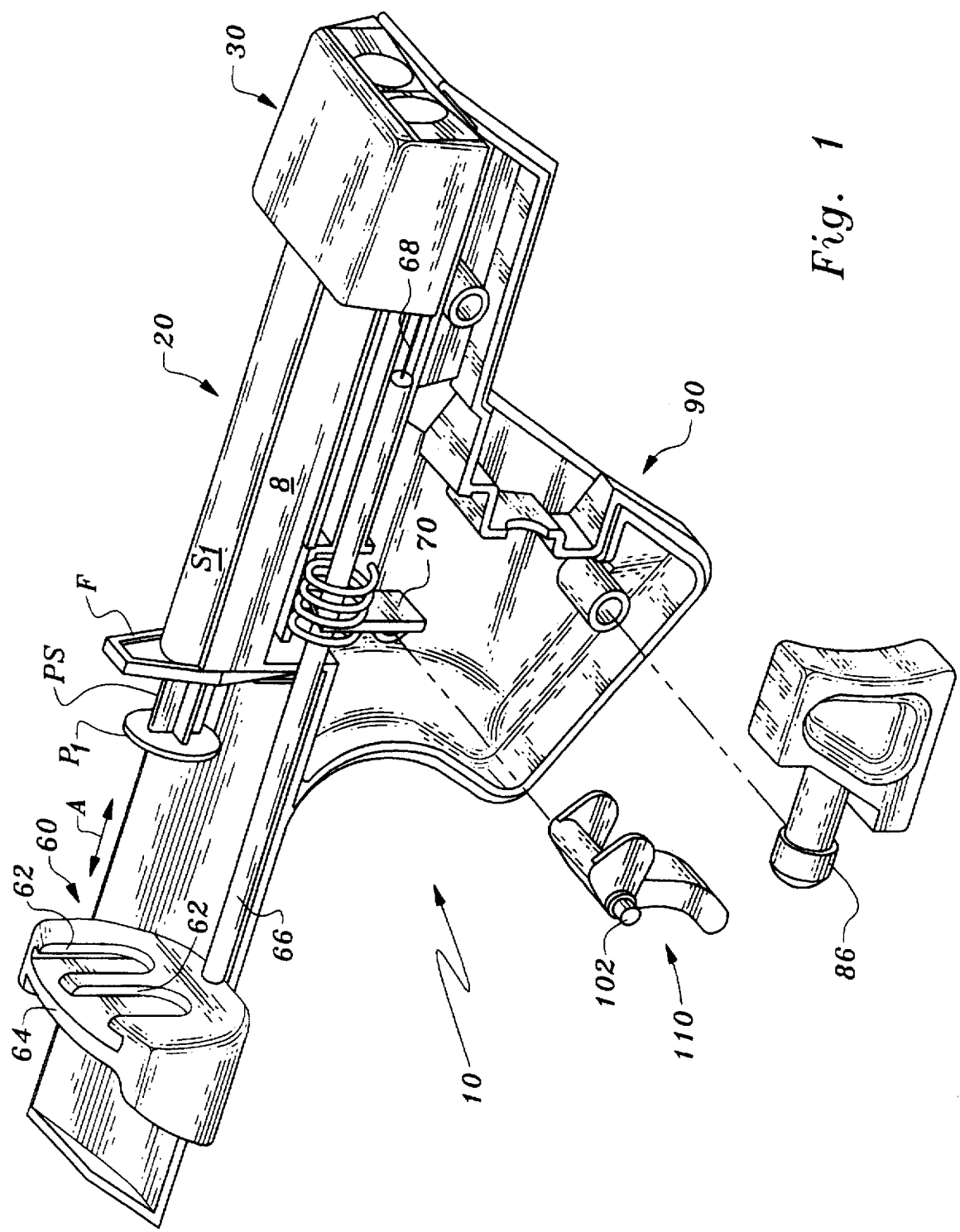
FIG. 1 is a perspective view partially exposing an interior portion of the sprayer according to the present invention.

Referring to the drawings, wherein like reference numerals denote like parts throughout the various drawing figures, reference numeral 10 is directed to the spray gun according to the present invention.

Figure 2:
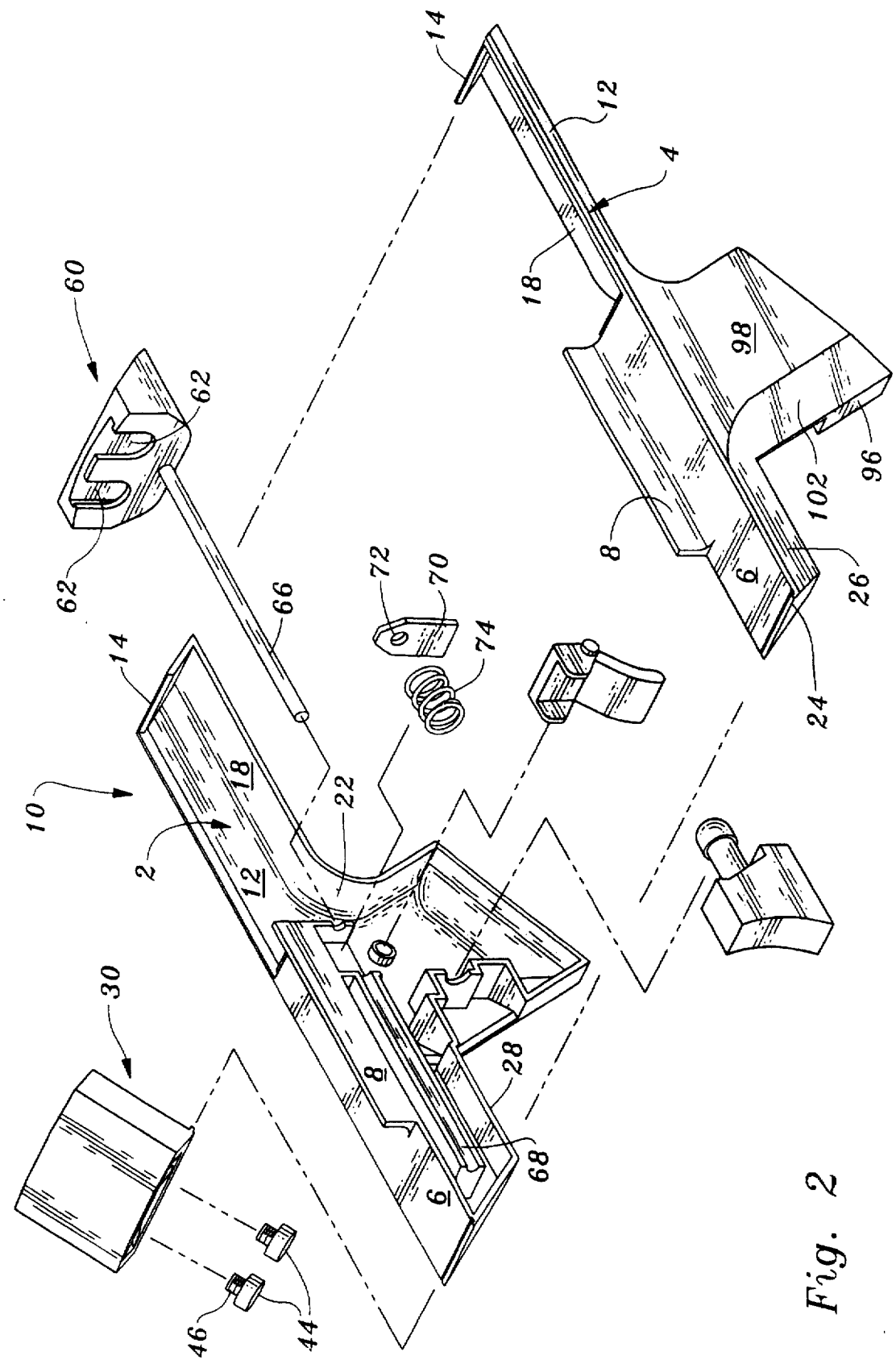
FIG. 2 is a an exploded parts perspective of that which is shown in FIG. 1.
Figure 5:
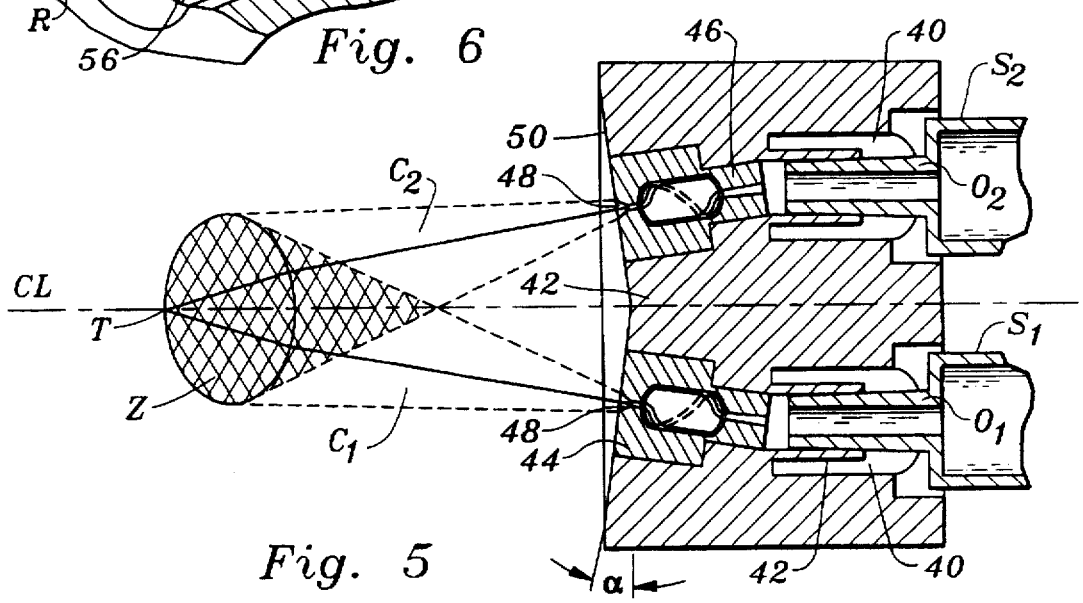
FIG. 5 is a sectional view taken along lines 5—5 of FIG. 4.

In its essence, and referring to FIGS. 1, 2 and 7, the spray gun 10 includes a barrel area 20 which can accommodate a pair of syringes S1, S2, each of which has plungers P1, P2 which can reciprocate within a hollow of the syringe body between a first contracted position (e.g. FIG. 1) to a second extended position (e.g. FIG. 7). The barrel includes, at opposed extremities, a tip area 30 at one end adapted to dock with each outlet of syringes S1, S2 and, at a remote extremity of the barrel 20, a plunger constraining means 60. As the plunger constraining means 60 includes means to engage each of the plungers P1, P2 of the syringes S1, S2 movement of the plunger constraining means and advancing the plunger along the direction of the double ended arrow "A" causes the plunger to reciprocate within the bore of syringes S1, S2. As the plunger pushes material out of syringes S1, S2, it is ejected from the tip 30 in two fine sprays. A combined pistol grip and trigger area 90 is shown in the figures which forms a lower portion of the spray gun 10. Motion of the trigger 80 in the direction of the double ended arrow "A" causes reciprocation through a linkage which amplifies the force applied to the trigger and advances the plunger along the direction of the double ended arrow "A" in a similar manner. As shown in FIG. 5, once the trigger has been actuated, a finely atomized mist or spray is effortlessly educed from the contents of each of syringes S1, S2 via the outlet tip 30, and a first and second fine mist, outwardly diverging and conical in shape, are provided. The mists are oriented such that each outwardly diverging conical spray converges to allow mixing the sprays and therefore the contents of the two syringes S1, S2. The dispensing surgeon enjoys ergonomic efficiencies and control over a powerfully delivered mist.

More specifically, and referring to FIGS. 1 and 2, the device 10 is shown as having two major housings, a first housing 2 and a second housing 4. Each housing is substantially the mirror image of the other and therefore minor difference (e.g. male and female frictional fittings) will not be belabored so as not to obscure clarity. The two housings are separable along a vertical plane which runs along the center line of the device.

The barrel portion 20 of each housing includes a planar shelf 6 which underlies the tip 30, an upwardly extending medial wall 8 which separates the first syringe S1 from the second syringe S2 and, at a rearward portion a recessed area including a peripheral wall 12 and an end wall 14. The peripheral wall 12 and the end wall 14 serve as a well within which the plungers P1, P2 of the syringes S1, S2 can be placed with accommodation for the finger grip area F of the syringe.

That is, a recess 16 (FIG. 7) that is formed by a barrier 17 spaced from the front shelf 6 and above a bottom wall 18 of the well secures the syringe in place particularly when the outlets O1, O2 of the syringes S1, S2 are nested within the tip 30 (FIG. 3) (to be described in greater detail) and a plunger ends P1, P2 of the syringes S1, S2 addresses the plunger constraining means 60 (to be described). The bottom wall 18 transitions to the pistol grip area 90 by means of an arcuate wall 22 (FIG. 7) having a radius of curvature which provides ergonomic benefit to the bight area of the hand of a user between the thumb and fore finger (FIG. 15).

The arcuate transition 22 terminates in a pistol grip end wall 92 that receives the topmost portion of the palm of the hand of a user adjacent the bight portion. The pistol grip area terminates in a bottom wall 94 (FIG. 7) which leads to a front wall 96. The dimension of the front wall 96 is such that it allows the middle finger of the user to rest comfortably thereon with the index finger of the user comfortably residing on the trigger 80. The remaining two fingers of the user fold comfortably under the bottom wall 94 of the pistol grip so that the lessened dimension of the pistol grip 90 allows access to areas of tight clearance.

The pistol grip further includes side walls 98 and a leading edge thereof may have a chamfered contour 102 (FIG. 2) to provide a smooth transition to an underside of the tip support area shelf 6. More particularly, the shelf 6 has a rearwardly canting leading face 24 which underlies the shelf 6 and communicates with the chamfered contour 102 via a side panel 26. Bottom wall 28 seals the front of the sprayer 10. The front wall 24 and side wall 26 are closed at a bottommost portion thereof with the bottom wall 28. The area above the trigger and below the barrel within the sprayer housing includes a linkage for advancing the plunger and amplifying the effect of motion of the trigger 80 as will be described. It is preferred that each of the housings 2, 4 be formed from moldable material such as plastic and be of durable construction, but can be economically manufactured so that the device can either be disposable or autoclavable.

Figure 3:
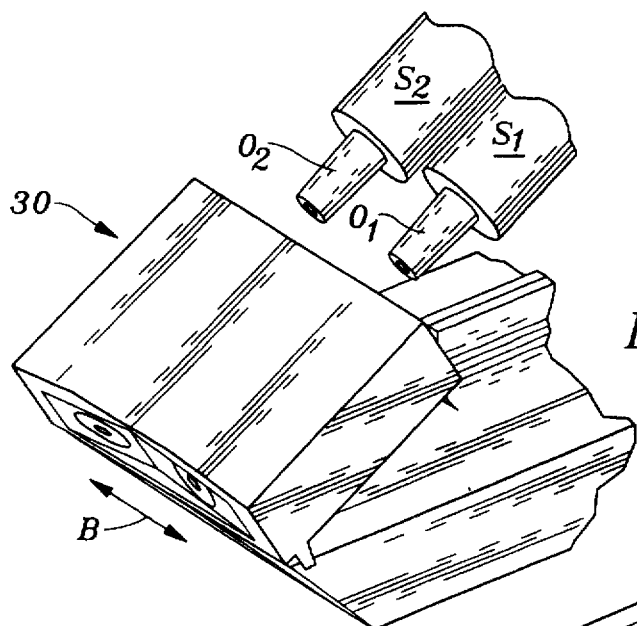
FIG. 3 is a perspective view of a tip portion of the device showing first and second syringes docking with the tip.
Figure 4:
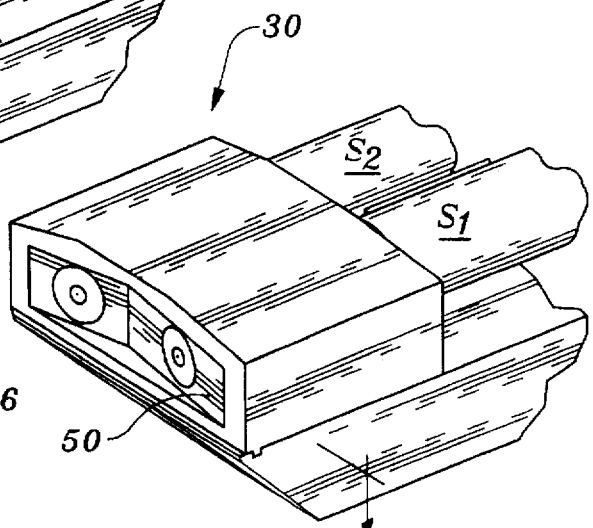
FIG. 4 is a perspective view similar to FIG. 3 showing the tip in a closed, deployed position.
Figure 6:
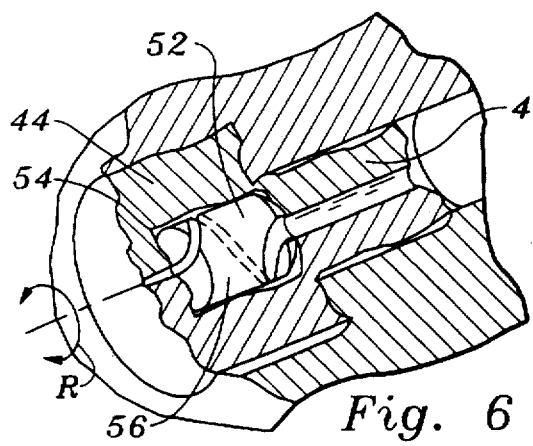
FIG. 6 is an exploded detail of a portion of the tip and atomizing spray head shown in FIG. 5.

As shown in FIGS. 3 and 8, the tip 30 can move from a first position (FIG. 8) to a second position (FIG. 3) which allows the syringe outlets O1, O2 access to the tip 30. More particularly, the top shelf 6 includes a recess 32 that provides a pivotal and frictional fit with the tip 30. The tip has a substantially J-shaped projection 34 that is complementally received within the recess 32. This defines a pivot point PP where a toe of the J underlies a projection 36 on a leading edge of the shelf 6.

A friction interference fit exists between the tip 30 and a portion of the J remote from the toe and is shown as reference numeral 38. This interference fit 38 between the tip 30 and its underlying support precisely locates the tip when in a deployed (e.g. FIG. 15) position.

To load the syringes into the spray gun 10, the tip 30 is shown in the upwardly deployed position of FIG. 3 and the outlets O2, O1 of syringes S2, S1 are disposed within receiving apertures 40 carried in the tip (FIG. 5). Once the tip 30 is in the FIG. 4 position, the front portion of the device is operable and ready for use. FIGS. 3 through 6 show details of the tip geometry.

Each outlets O1, O2 commonly referred to as a luer coupling. The luer coupling has a conical taper, growing smaller as it extends away from the body of the syringe and is adapted to frictionally reside within a complementally formed opening 40. A sleeve 42 in tangential registry with the outlets O1, O2 receive the syringes S1, S2. Thus, the sleeve 42 may have a taper parallel to the taper of the luer coupling so that it diverges outwardly to receive the luer coupling.

Each syringe communicates with its own atomizing nozzle 44. Each atomizing nozzle 44 has a stem 46 (FIGS. 2, 5, 6) having a lesser diameter than the front portion 44 which registers on a front face 50 of the tip block 30. Each of the nozzles 44 are oriented with respect to a center line CL (FIG. 5) so that the nozzles point towards a common target T approximately 2.56 inches away from the nozzles 44. Thus, each nozzle delivers a substantially conical spray C1, C2 that diverges from a nozzle outlet 48. A zone Z of fibrin glue is thus provided at the target T.

An interior portion of the nozzle body includes atomizer 52 contained within a bore 54 formed within the front portion 44 of the nozzle. The atomizer 52 has an exterior groove 56 causing the atomizer 52 to rotate in the direction of the double ended arrows "R". This helps break up the liquid coming from the syringe to form a fine mist. The grooves 56 on the atomizer 52 allow the atomizer to rotate within the complementally formed recess and provide additional agitation to the mixture coming out.

As shown in FIG. 5, this structure allows two very fine mists to diverge from the nozzle outlet 48. Having the nozzles 44 canted towards each other allows focused mixing a discrete distance from the nozzles so that when thrombin is used in one syringe and fibrinogen is used in the other syringe, there is a zone Z of overlap that allows good mixing of the two components without either of the components touching the other near a nozzle outlet. This prevents clogging.

Note, however, in the unlikely event that should a clog occur, the tip 30 can be easily removed by overcoming the friction of the J-type hinge of FIG. 8 by moving the tip 30 along the direction of the double ended arrow "B" shown in FIG. 3. This allows a new tip 30 to replace an old one. Note also (FIG. 5) that the front wall 50 of the tip is recessed at its vertical center and subtends an arc defined by an angle α which preferably can be fifteen degrees, but can vary from one to forty-five degrees.

As shown in FIG. 7, a plunger constraining means 60 is located at an end of the barrel 20 remote from the tip 30. The plunger constraining means includes a pair of upwardly opening U-shaped slots 62 (FIGS. 1 and 2) having a dimension adapted to receive a free end of the plungers P1, P2 normally engaged by a thumb of the user. The thumb engaging area is substantially disc-shaped and slides within the U-shaped slot 62 so that the shaft of the piston PS is on one side of the U-shaped slot and the disc part of the piston is on another. Please see FIGS. 7 and 15.

As shown, clearance is provided between a back wall of the plunger 64 and the U-shaped slots 62 to accommodate the disc part of the plunger. Each syringe is located on opposite sides of the vertical plane of symmetry of the device. The plunger 60 has a relatively large mass and rides within the well at a rear portion of the barrel described hereinabove. The plunger 60 has a contour substantially complemental to the well so that it slides in the well comfortably without binding. This also allows a single syringe to be used in a stable manner without fear of binding because of the support afforded between the walls of the well and the plunger 60.

A bottom portion of the plunger forward of the slots 62 includes a plunger rod 66. One end of the plunger rod 66 is attached to the plunger constraining means or plunge pusher 60 and another end reciprocates within a bore 68 formed from the housings 2, 4 and shown in FIGS. 1, 2 and 7. The bore 68 is formed from arcuate semi-cylindrical sections each formed on inner surfaces of the housing 2, 4 and provide further smooth response to the user when the plunger is being manipulated.

The plunger is activated by the trigger 80. The sequence of steps involving the plunger and trigger can be considered when viewing FIGS. 9 through 14. Briefly, a wobble plate 70 is configured with a hole 72 at an upper portion thereof dimensioned to just pass over the rod 66. The wobble plate 70 is constrained to reside most of the time in a position nearest the bight area 22 of the handle by means of a spring 74 carried within a spring cavity 76 formed on an under side of the barrel shelf 6. The spring 74 is captured on one side by a web 78 formed in the housing. Bore 68 and rod 66 pass through a web aperture. On another end of the spring cavity 76, adjacent the bight area 22, a second apertured web 82 keeps the wobble plate 70 thereagainst by virtue of the spring 74 pressing against a face of the wobble plate 70.

The trigger 80 includes a stem portion 84 that terminates in a bulbous shaped trigger bearing surface 86. The pistol grip portion of the housing adjacent the trigger has an exterior contour complemental to the trigger and includes a limit stop 88 at upper and lower portions to precisely locate an abutment against which the trigger 80 can go no further. This provides assurance to the surgeon that there is no chance of "overshooting", i.e., over dispensing too much fibrin glue as in the prior art. Clearance is provided on the trigger 80 by a canted portion 89 that allows the trigger stem 84 to reciprocate along the direction of the double ended arrow "A".

The bulbous portion of the trigger 86 pushes against pivot lever 110. Pivot lever 110 has a pivot 102 that allows pivotal motion of the lever 110 in the direction of the double ended arrow "D" of FIG. 9. The lever 110 includes a first leg 104 on one side of the pivot 102 driven by the bulbous end 86 of the trigger 80. A second leg 106, located on pivot lever 110 on an opposite side of pivot 102 contacts a face of the wobble plate 70 remote from the spring 74.

FIG. 10 shows the "neutral" angular relationship of the wobble plate 70 to its hole 72 vis-a-vis the plunger rod 66. In FIG. 11, the trigger 80 is moved in the direction of arrow "A1". This moves pivot lever 110 along D1. In FIG. 12, wobble plate 70 moves in direction D3 and two points 70a and 70b of the wobble plate 72 bite onto the plunger rod 66 causing motion of the plunger rod in the direction "A2".

FIGS. 13 and 14 show the trigger 80 being relaxed and allowed to assume an at rest position again and occurs just after having released the trigger of FIG. 11. The trigger 80 now moves along arrow "A3" of FIG. 13 by pressure from spring 74. The wobble plate 70 has two other edges 70c and 70d defined by the hole 72 that also bite against the plunger rod 66. This causes slight return of the plunger rod, but only a minute distance A4. The effect of this minute return or "creep back" assures that the plungers P1, P2 on the syringes S1, S2 move back in a similar direction, but only a short distance. This provides a slight negative pressure in the nozzles 44 of the tip 30. This prevents the contents within the syringe from dribbling out, further making nozzle clogging less likely.

Having thus described the invention, it should be apparent that numerous structural modifications and adaptations may be resorted to without departing from the scope and fair meaning of the instant invention as set forth hereinabove and as described hereinbelow by the claims.

We claim:

1. A gun for dispensing fibrin glue formed from thrombin and fibrinogen, where both the thrombin and the fibrinogen are respectively sequestered in independently operable syringes, the syringes each having a plunger which reciprocates within a hollow of a body of the syringe and an outlet on the syringe body remote from the plunger, said gun comprising in combination:

a barrel, means for supporting each of the syringes on said barrel of said gun, means for constraining the plungers of each syringe to control each plunger's reciprocation within its syringe, said plunger constraining means operatively coupled to a trigger located on a handle said handle attached to said barrel metering means between said trigger and said plunger's constraining means to control the degree to which the plungers are depressed within the hollows of the syringes to thereby precisely meter the outflow from each syringe such that a standardized quanta of fibrinogen and thrombin are dispensed with each trigger pull, and first and second dispensing means on said barrel, one for each syringe, said dispensing means operatively coupled to the outlets of their respective syringes whereby motion of the plungers by said trigger dispenses the contents of each said syringe.

2. The gun of claim 1 wherein said metering means includes a shaft having first and second ends, said shaft coupled to said trigger at said first end and said shaft second end in operative registry with a pivot lever, said pivot lever pivotally coupled to a wobble-plate, said wobble-plate having a bore to receive therethrough a rod, said rod coupled to said plunger constraining means, and a biasing means operatively coupled between said rod and said wobble plate such that upon squeezing and thereafter releasing said trigger, said trigger and said wobble-plate return to an initial, ready position and said plunger constraining means relaxes pressure on the syringes to prevent inadvertent dispensing of the thrombin and fibrinogen.

3. The gun of claim 2 wherein said dispensing means are spray nozzles on said barrel.

4. The gun of claim 3 wherein said spray nozzles are angled toward each other so that fluid dispelled from the syringes through said nozzles will communicate while airborne.

5. The gun of claim 4 wherein said handle further comprises:
a first finger rest, said trigger adjacent to and interposed between said barrel and said first finger rest,
a bottom wall adjacent said first finger rest and opposite said trigger and said bottom wall including a second finger rest.

6. The gun of claim 5 wherein said handle has a palm rest adjacent to and interposed between said bottom wall and said barrel, forming an area at the intersection of said barrel and said palm rest to accommodate a bight portion of a user's hand between a thumb and index finger.

7. The gun of claim 6 further comprising a trigger housing juxtaposed complementarily about said trigger.

8. The gun of claim 7 wherein said trigger comprises:
top and bottom sides, said bottom side longer than said top side, and
front and rear sides, said front side concavically formed to better receive an index finger, said rear side complimentarily formed to coact with said trigger housing.

9. The gun of claim 8 wherein said trigger and said first finger rest surface are substantially parallel to said palm rest.

10. The gun of claim 9 wherein said trigger and said first finger rest surface are substantially perpendicular to said second finger rest surface.

11. The gun of claim 10 wherein said trigger and said first finger rest surface are obtusely angled from said barrel.

12. The gun of claim 11 wherein said biasing means is a spring through which rides said rod and against, said spring straddles said wobble-plate and an abutment.

13. A method for forming fibrin glue, the steps including:
sequestering thrombin in a first syringe,
sequestering fibrinogen in a second syringe,
orienting each said syringe to be in fluid communication with its own dispensing head,
coupling plungers of each said syringe to a trigger, and
metering a defined quantum exiting each syringe by squeezing the trigger each said squeeze of the trigger controlling the metering.

14. The method of claim 13 further including the step of forming a first and second conical spray mist upon projection from each dispensing head.

15. The method of claim 14 including orienting each conical spray mist to converge at a fixed distance from each dispensing head, allowing each mist to commingle en route to a target.

16. The method of claim 15 including forming said dispensing heads as spray nozzles.

17. The method of claim 16 including housing said fibrinogen source and said thrombin source in a barrel.

18. The method of claim 17 including forming a handle to project from said barrel.

19. The method of claim 18 including forming a trigger in said handle so that the launching source is activated by triggering said trigger.

20. The method of claim 19 including pressing and releasing said trigger, wherein said thrombin and said fibrinogen are launched and projected upon pressing said trigger, thereby precisely metering the outflow from each syringe such that a standardized quanta of fibrinogen and thrombin are dispensed with each trigger pull.

21. Fibrin glue formed from mixing two fine mists, the steps including:
projecting each mist from a syringe conically outwardly such that each mist overlaps the other a set distance from its launching source, the fibrin glue formed by:
a first said mist of thrombin sprayed as an atomized mist in a first outwardly diverging conical pattern from a thrombin source, and
a second said mist of fibrinogen sprayed in a second outwardly diverging conical pattern,
said first and second outwardly diverging conical patterns overlapping each other during a portion of the respective trajectories remote from their launching sources so that the thrombin and fibrinogen can mix while aloft and land on a target in a substantially overlapping conical pattern as fibrin glue.

22. The glue of claim 21 wherein the thrombin and fibrinogen are dispensed in substantially equal volumes.

23. A medicament dispenser, comprising, in combination:
a barrel having means to support and means to deliver medicament,
a handle coupled to said barrel, said handle having a first finger rest,
a trigger adjacent to and interposed between said barrel and said first finger rest, said trigger coupled to said medicament delivery means, and
said handle having a bottom wall adjacent said first finger rest and opposite said trigger, said bottom wall defining a second finger rest.

24. The medical dispenser of claim 23 wherein said handle has a palm rest adjacent to and interposed between said bottom wall and said barrel, forming an area at the intersection of said barrel and said palm rest to accommodate a bight portion of a user's hand between a thumb and index finger.

25. The medical dispenser of claim 24 further comprising a trigger housing juxtaposed complementarily about said trigger.

26. The medical dispenser of claim 25 wherein said trigger comprises:
top and bottom sides, said bottom side longer than said top side, and
front and rear sides, said front side concavically formed to better receive an index finger, said rear side complementarily formed to coact with said trigger housing.

27. The medical dispenser of claim 26 wherein said trigger and said first finger rest surface are substantially parallel to said palm rest.

28. The medical dispenser of claim 27 wherein said trigger and said first finger rest surface are substantially perpendicular to said second finger rest surface.

29. The medical dispenser of claim 28 wherein said trigger and said first finger rest surface are obtusely angled from said barrel.

30. A dispenser for delivering medicament contained in a syringe, comprising, in combination:
a barrel,
a dispensing head on said barrel,
support means for the syringe on said barrel including means to depress a plunger of the syringe into a cavity of the syringe, the syringe having an outlet coupled to said dispensing head,
said dispenser including a hand grip connected to said barrel,
a trigger on said hand grip,
a rod extending from said depressing means, and
a wobble-plate extending from said trigger to said rod, such that squeezing said trigger pushes the plunger into the syringe cavity my moving said wobble-plate and said rod.

31. The medicament delivery dispenser of claim 30 wherein said dispensing head includes a spray nozzle on said barrel.

32. The medicament delivery dispenser of claim 31 wherein said hand grip further comprises:
   a first finger rest, said trigger adjacent to and interposed between said barrel and said first finger rest,
   a bottom wall adjacent said first finger rest and opposite said trigger and said bottom wall including a second finger rest.

33. The medicament delivery dispenser of claim 32 wherein said hand grip has a palm rest adjacent to and interposed between said bottom wall and said barrel, forming an area at the intersection of said barrel and said palm rest to accommodate a bight portion of a user's hand between a thumb and index finger.

34. The medicament delivery dispenser of claim 33 further comprising a trigger housing juxtaposed complementarily about said trigger.

35. The medicament delivery dispenser of claim 34 wherein said trigger comprises:
   top and bottom sides, said bottom side longer than said top side, and
   front and rear sides, said front side concavically formed to better receive an index finger, said rear side complimentarily formed to coact with said trigger housing.

36. The medicament delivery dispenser of claim 35 wherein said trigger and said first finger rest surface are substantially parallel to said palm rest.

37. The medicament delivery dispenser of claim 36 wherein said trigger and said first finger rest surface are substantially perpendicular to said second finger rest surface.

38. The medicament delivery dispenser of claim 37 wherein said trigger and said first finger rest surface are obtusely angled from said barrel.

39. The medicament delivery dispenser of claim 38 wherein said wobble-plate is pivotally coupled to said trigger.

40. The medicament delivery dispenser of claim 39 wherein moving said wobble-plate includes arcuately rocking said wobble-plate about said pivot upon squeezing said trigger.

41. The medicament delivery dispenser of claim 40 wherein moving said rod includes incrementally advancing said rod upon successive trigger squeezing and releasing.

* * * * *